US009333338B2

(12) United States Patent
Dhanasingh et al.

(10) Patent No.: US 9,333,338 B2
(45) Date of Patent: May 10, 2016

(54) ELECTRODE FOR COMMON CAVITY COCHLEAR MALFORMATION

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT); Rocco Calabrese Gac, Santiago (CL)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/512,156

(22) Filed: Oct. 10, 2014

(65) Prior Publication Data
US 2015/0105794 A1    Apr. 16, 2015

Related U.S. Application Data

(60) Provisional application No. 61/890,927, filed on Oct. 15, 2013.

(51) Int. Cl.
A61N 1/05       (2006.01)
A61B 17/00      (2006.01)

(52) U.S. Cl.
CPC ..... A61N 1/0541 (2013.01); A61B 2017/00787 (2013.01)

(58) Field of Classification Search
CPC .......................... A61N 1/0541; A61N 1/36032
USPC .............................................. 607/55–57, 137
See application file for complete search history.

(56) References Cited

U.S. PATENT DOCUMENTS

| 5,545,219 A * | 8/1996 | Kuzma | ..................... A61N 1/05 607/137 |
| 5,645,585 A * | 7/1997 | Kuzma | ................. A61F 11/004 607/137 |
| 6,070,105 A * | 5/2000 | Kuzma | ................. A61N 1/0541 607/137 |
| 6,195,586 B1 * | 2/2001 | Kuzma | ................. A61N 1/0541 607/137 |

(Continued)

FOREIGN PATENT DOCUMENTS

EP        0818123        1/2003

OTHER PUBLICATIONS

International Searching Authority, Authorized Officer Shane Thomas, International Search Report and the Written Opinion—PCT/US14/60146, date of mailing Mar. 25, 2015, 15 pages.

Primary Examiner — Eugene Wu
(74) Attorney, Agent, or Firm — Sunstein Kann Muphy & Timbers LLP

(57) ABSTRACT

A method is described to implant a cochlear implant electrode into a cochlea having a single internal cavity defined by an outer cavity wall. An implantable electrode array is made of a resilient electrode carrier material and has an outer surface with one or more stimulation contacts for delivering the electrical stimulation signals to adjacent neural tissue. A distal end of the electrode array is attached to an insertion line made of a line material different from the electrode carrier material. The distal end of the electrode array is inserted through a single cochleostomy opening into the cochlea while an extra-cochlear end of the insertion line is held outside the cochleostomy opening. The remainder of the electrode array is inserted through the cochleostomy opening into the cochlea while continuing to hold the extra-cochlear end outside the cochlea to maneuver all of the stimulation contacts against the outer cavity wall.

5 Claims, 6 Drawing Sheets

(56) References Cited

U.S. PATENT DOCUMENTS

| | | | |
|---|---|---|---|
| 6,374,143 B1* | 4/2002 | Berrang | A61N 1/0541 600/379 |
| 6,498,954 B1* | 12/2002 | Kuzma | A61N 1/0541 607/137 |
| 7,442,164 B2 | 10/2008 | Berrang et al. | |
| 8,150,528 B2 | 4/2012 | Jolly | |
| 2003/0171758 A1 | 9/2003 | Gibson et al. | |
| 2004/0078057 A1* | 4/2004 | Gibson | A61M 31/002 607/3 |
| 2011/0106101 A1* | 5/2011 | Tortonese | A61N 1/0541 606/129 |
| 2011/0288468 A1 | 11/2011 | Dadd et al. | |
| 2012/0185028 A1 | 7/2012 | Gantz | |
| 2013/0138117 A1 | 5/2013 | Abbott et al. | |
| 2015/0105795 A1* | 4/2015 | Lenarz | A61N 1/0541 606/129 |

* cited by examiner

US 9,333,338 B2

ELECTRODE FOR COMMON CAVITY COCHLEAR MALFORMATION

This application claims priority from U.S. Provisional Patent Application 61/890,927, filed Oct. 15, 2013, which is incorporated herein by reference.

FIELD OF THE INVENTION

The present invention relates to medical implants, and more specifically to an implantable electrode for use in cochlear implant systems in patients having a malformed cochlea.

BACKGROUND ART

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an implanted electrode carrier 110. Typically, this electrode carrier 110 includes multiple electrodes on its surface that provide selective stimulation of the cochlea 104.

In some persons, the cochlear shape fails to develop properly and various malformation conditions can occur such as those shown in FIG. 2: cochlear aplasia, cochlear hypoplasia, common cavity (CC) malformation, and incomplete partitioning. Specifically in a common cavity malformation the cochlea and the vestibule are represented by a single chamber. This structure may have cochlear and vestibular neural structures, but it completely lacks inter-scala separation (no basilar membrane), no modiolus trunk, and it appears as a single cavity. The neural structures are believed to be present at the bony capsule defining the outer cavity wall. The specific size of the cavity can vary significantly and can be measured using medical imaging.

Placing an electrode inside a malformed common cavity cochlea is not straightforward and needs utmost care to ensure that the stimulation contacts are either touching or very close to the outer wall of the cavity. The current technique involves making two cochleostomy openings in the outer surface of the cochlea for the electrode placement, which is undesirably traumatic.

FIG. 3A shows one approach wherein the electrode array 302 has an extended distal end. Two cochleostomies 304 are made in the outer surface of the cochlea 300, the electrode array 302 is inserted through one of the cochleostomies 304, and the distal tip of the electrode array 302 is retrieved and pulled through the other cochleostomy 304. The surgeon has to manipulate the electrode array 302 to attempt to place the stimulation contacts 303 against the outer wall 301 of the cavity, after which the final position of the electrode array 302 is fixed and the distal extension may be removed.

FIG. 3B shows another approach for electrode implantation in a common cavity, again requiring two cochleostomies 304 in the outer surface of the cochlea 300. Two separate electrode arrays 302 are used, one through each cochleostomy 304, and again considerable surgical skill is needed to manipulate the electrode arrays 302 to place their stimulation contacts 303 adjacent to the outer wall 301 of the cavity. Both techniques are highly traumatic in requiring two cochleostomies and both require considerable surgical skill to be effective.

SUMMARY OF THE INVENTION

Embodiments of the present invention are directed to a method of implanting a cochlear implant electrode into a cochlea having a single internal cavity defined by an outer cavity wall (e.g., a malformed common cavity cochlea). An implantable electrode array is made of a resilient electrode carrier material and has an outer surface with one or more stimulation contacts for delivering the electrical stimulation signals to adjacent neural tissue. A distal end of the electrode array is attached to an insertion line made of a line material different from the electrode carrier material. The distal end of the electrode array is inserted through a single cochleostomy opening into the cochlea while an extra-cochlear end of the insertion line is held outside the cochleostomy opening. The remainder of the electrode array is inserted through the cochleostomy opening into the cochlea while continuing to hold the extra-cochlear end outside the cochlea to maneuver all of the stimulation contacts against the outer cavity wall.

The insertion line may be configured to be cut after feeding the electrode array into the cochlea so that no part of the insertion line remains within the cochleostomy opening. The electrode array may be fed through the cochleostomy opening until the distal end of the electrode array contacts the outer cavity wall opposite the cochleostomy opening. Then after the distal end of the electrode array contacts the outer cavity wall, the insertion line may be retracted back through the cochleostomy opening while continuing to feed the electrode array through the cochleostomy opening until the distal end of the electrode array reaches the cochleostomy opening. The distal end of the electrode array may include an attachment ring to which the insertion line is attached. The line material may be a medical grade suture material.

Embodiments of the present invention also include a corresponding implantable electrode. An extra-cochlear electrode lead contains signal wires for conducting electrical stimulation signals. An intra-cochlear electrode array is configured to be inserted into the cochlea through a single cochleostomy opening and is made of a resilient carrier material having an outer surface with one or more stimulation contacts for delivering the electrical stimulation signals to adjacent neural tissue. An insertion line is attached to a distal end of the electrode array and made of a line material different from the electrode carrier material. The insertion line is configured to have an extra-cochlear end extending outside the cochleostomy opening during surgical insertion of the electrode array into the cochlea.

In specific embodiments, the insertion line may be configured to be cut after feeding the electrode array into the cochlea so that no part of the insertion line remains within the cochleostomy opening. The distal end of the electrode array may include an attachment ring to which the insertion line is attached. The line material may be a medical grade suture material. Embodiments of the present invention also include a complete cochlear implant system having an electrode array according to any of the above.

DETAILED DESCRIPTION OF SPECIFIC EMBODIMENTS

Various embodiments of the present invention are directed to an implantable electrode for a common cavity cochlea having an insertion line at a distal end of the electrode array that is suitable for insertion into a malformed common cavity cochlea through a single cochleostomy opening. Because the electrode is configured for insertion through a single cochleostomy opening rather than requiring two cochleostomies as in existing conventional arrangements, the amount of trauma to the cochlea is reduced and an easier surgical insertion process can be used. And, the insertion line approach is suitable for using a conventional cochlear implant electrode without significant structural alteration or without special fabrication specifically for a common cavity cochlea.

Figure 1:
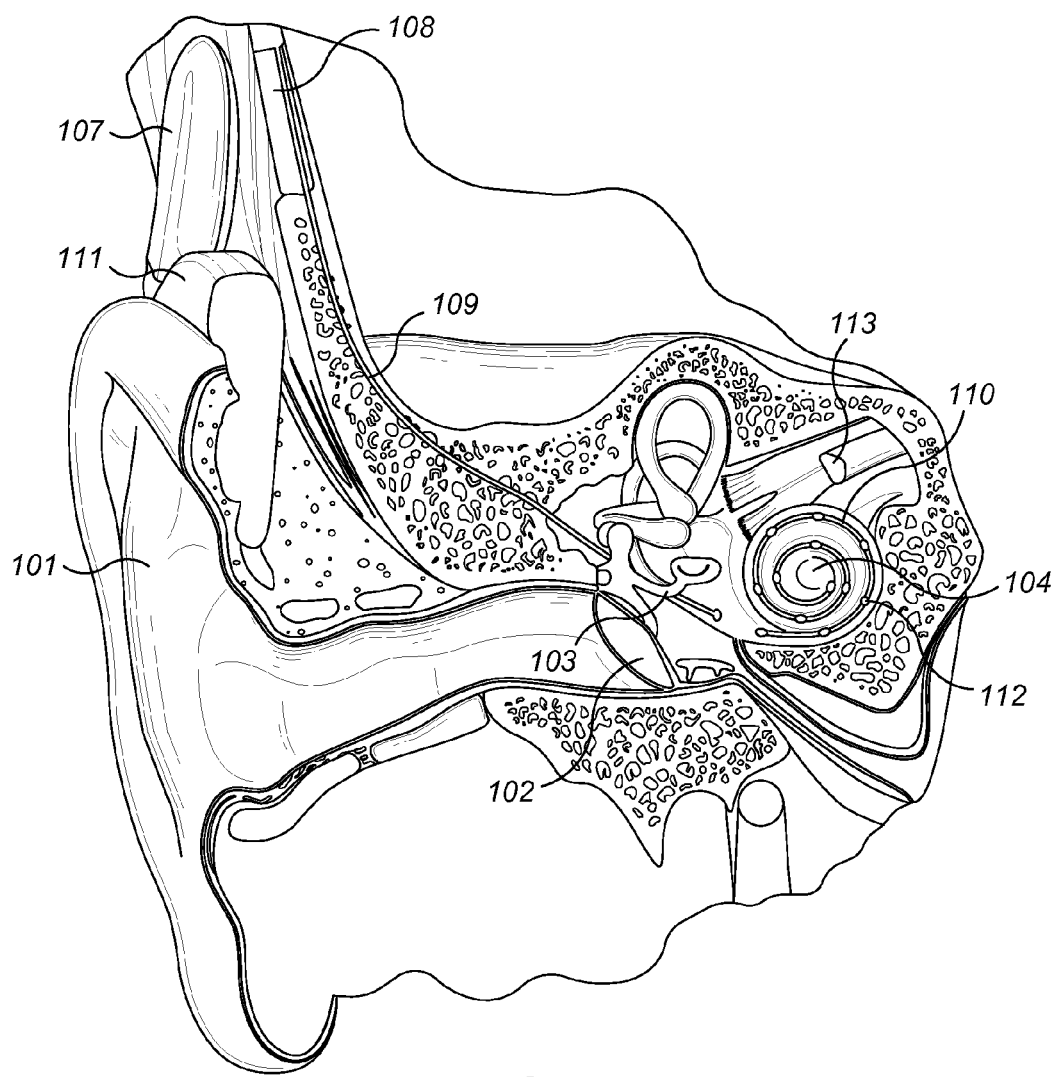
FIG. 1 shows elements of a human ear having a typical cochlear implant system.
Figure 2:
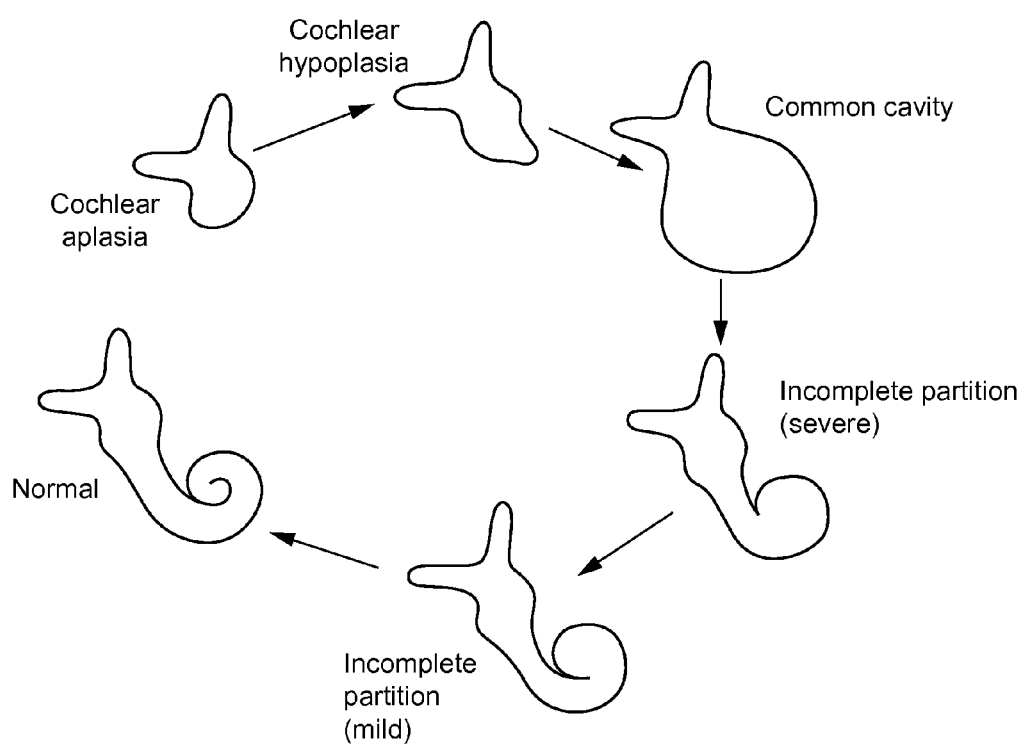
FIG. 2 illustrates various cochlear malformation shapes.
Figure 3A:
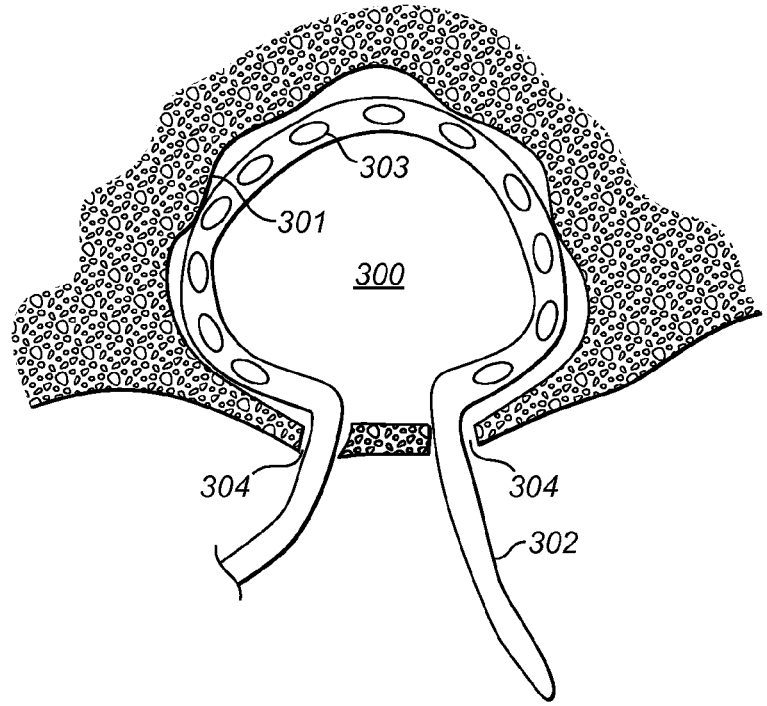
FIG. 3 A-B show conventional electrode insertion into a common cavity cochlea using two cochleostomies.
Figure 3B:
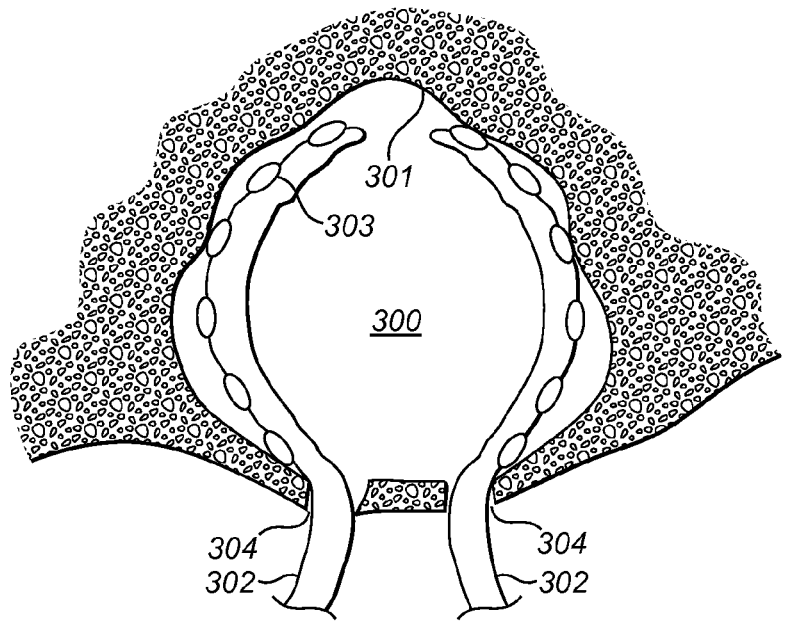
Figure 4A:
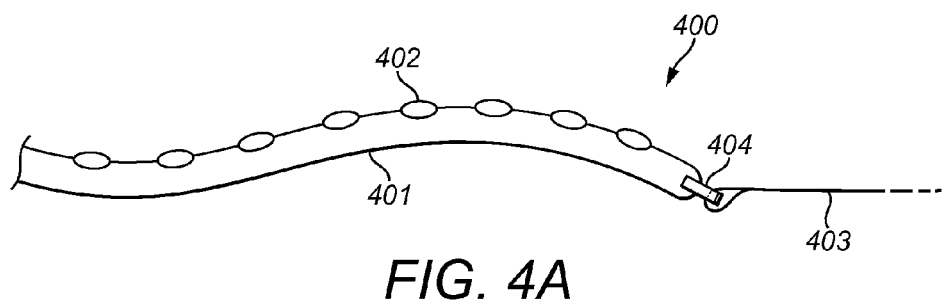
FIG. 4 A-B show a common cavity electrode having an insertion line according to an embodiment of the present invention.
Figure 4B:
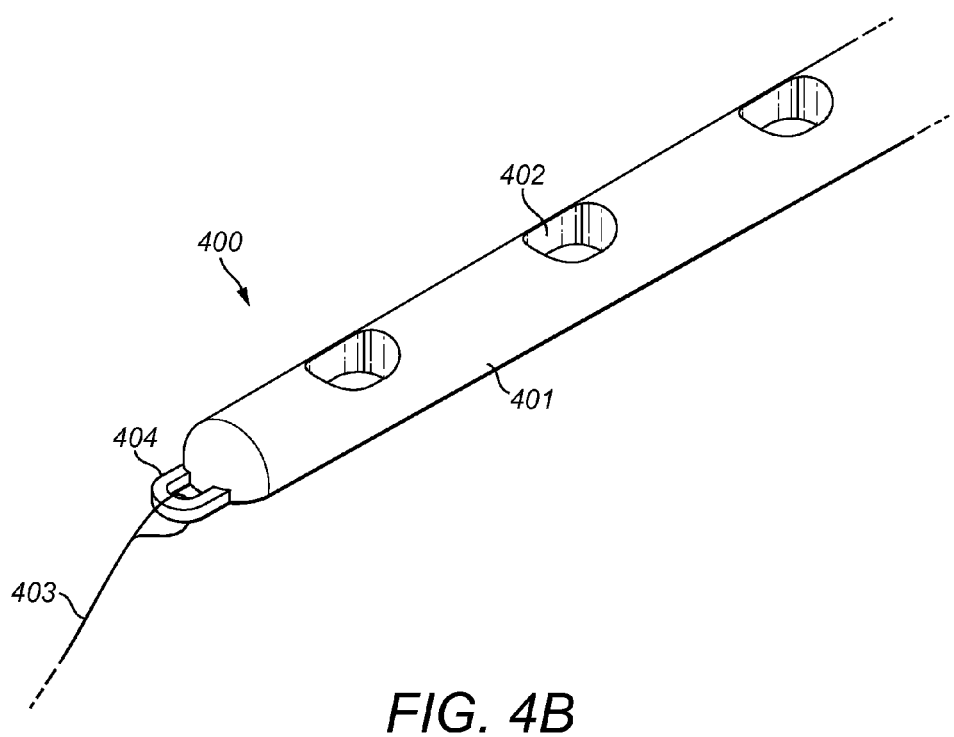

FIG. 4 A-B show an implantable common cavity electrode 400 according to one specific embodiment of the present invention. An extra-cochlear electrode lead (not shown) contains signal wires for conducting electrical stimulation signals to an intra-cochlear electrode array 401 made of a resilient carrier material (e.g., medical grade silicone). The outer surface of the electrode array 401 has one or more stimulation contacts 402 for delivering the electrical stimulation signals to adjacent neural tissue in the outer cavity wall of a malformed common cavity cochlea. The electrode array 401 is configured to be inserted into the cochlea through a single cochleostomy opening, thereby creating far less trauma and using a far simpler surgical technique.

An insertion line 403 is attached to a distal end of the electrode array 401 for example, by fixation to an attachment ring 404. The insertion line 403 is made of a line material different from the electrode carrier material; for example, medical grade surgical suture material. The insertion line 403 is long enough to have an extra-cochlear end that extends outside the cochleostomy opening during surgical insertion of the electrode array 401 into the cochlea, which is therefore well-suited to be fixedly held by the surgeon during the insertion process.

Figure 5A:
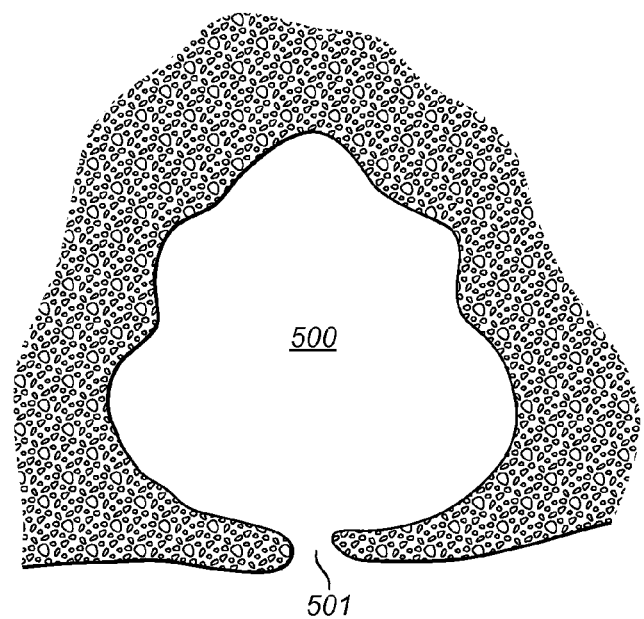
FIG. 5 A-D shows insertion of a common cavity electrode into a malformed common cavity cochlea.
Figure 5B:
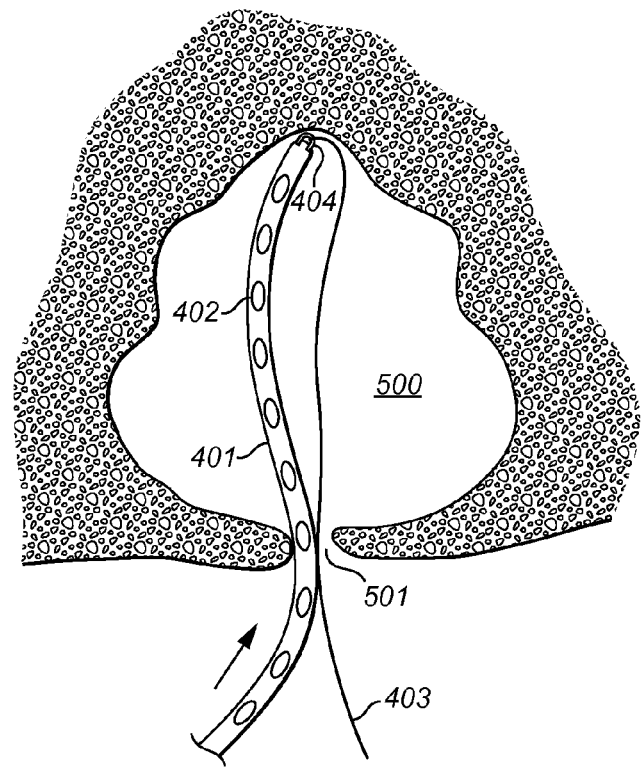
Figure 5C:
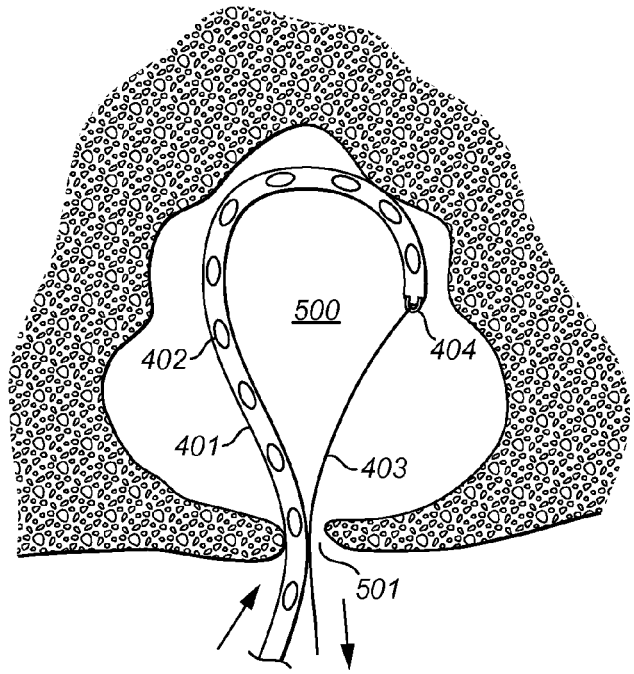
Figure 5D:
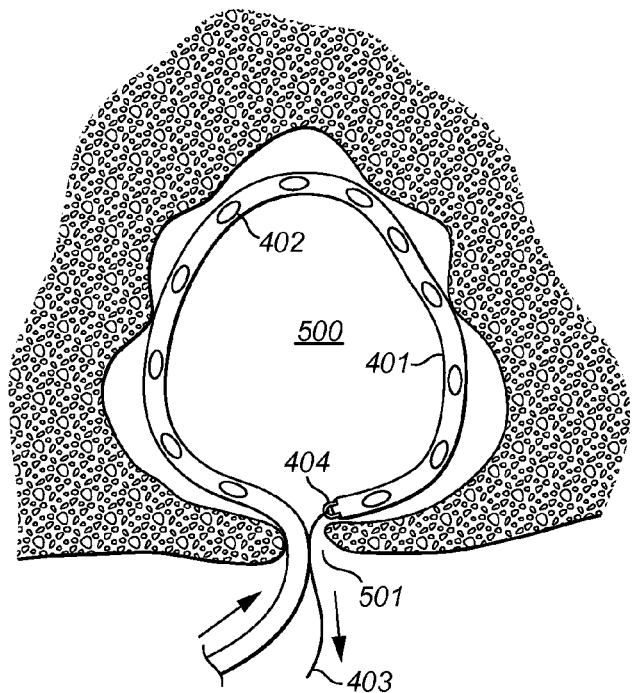

FIG. 5A shows a malformed cochlea having a single internal cavity 500 defined by an outer cavity wall (e.g., a malformed common cavity cochlea) having a single cochleostomy opening 501 for insertion of such an electrode array. The distal end of the electrode array 401 initially is inserted through the cochleostomy opening 501 into the internal cavity 500 of the cochlea while an extra-cochlear end of the insertion line 403 is securely held outside the cochleostomy opening 501. The electrode array 401 is fed through the cochleostomy opening 401 until the distal end of the electrode array 401 contacts the outer cavity wall of the internal cavity 500 opposite the cochleostomy opening 501, as shown in FIG. 5B. Then after the distal end of the electrode array 401 contacts the outer cavity wall, the insertion line 403 is retracted back through the cochleostomy opening 501 while continuing to feed the electrode array 401 through the cochleostomy opening 501 and while continuing to hold the extra-cochlear end of the insertion line 403 outside the cochlea. As the distal end of the electrode array 401 reaches the cochleostomy opening 501, as shown in FIG. 5D, the surgeon maneuvers all of the stimulation contacts 402 against the outer cavity wall of the internal cavity 500.

The specific lengths of the electrode array 401 and/or the insertion line 403 may differ in specific embodiments in order to accommodate different size internal cavities 500. And the insertion line 403 may be configured to be cut after fully feeding the electrode array 401 into the internal cavity 500 of the cochlea so that no part of the insertion line 403 remains within the cochleostomy opening 501 to avoid bacterial infection.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of implanting a cochlear implant electrode in a cochlea having a single internal cavity defined by an outer cavity wall, the method comprising:

inserting through a single cochleostomy opening a distal end of an implantable electrode array made of a resilient electrode carrier material and having an outer surface with one or more stimulation contacts for delivering electrical stimulation signals to adjacent neural tissue; wherein the distal end is attached to an insertion line made of a line material different from the electrode carrier material and configured to have an extra-cochlear end extending outside the cochleostomy opening during the inserting;

continuing to feed the electrode array through the cochleostomy opening into the cochlea while holding the extra-cochlear end outside the cochlea, until the distal end of the electrode array contacts the outer cavity wall opposite the cochleostomy opening, to maneuver all of the stimulation contacts against the outer cavity wall; and after the distal end of the electrode array contacts the outer cavity wall, retracting the insertion line back through the cochleostomy opening while continuing to feed the electrode array through the cochleostomy opening into the cochlea until the distal end of the electrode array reaches the cochleostomy opening.

2. The method according to claim 1, further comprising:
cutting the insertion line after feeding the electrode array into the cochlea so that no part of the insertion line remains within the cochleostomy opening.

3. The method according to claim 1, wherein the distal end of the electrode array includes an attachment ring to which the insertion line is attached.

4. The method according to claim 1, wherein the line material is a medical grade suture material.

5. The method according to claim 1, wherein the cochlea is a malformed common cavity cochlea.

* * * * *